US008551550B2

(12) United States Patent
Gautier et al.

(10) Patent No.: US 8,551,550 B2
(45) Date of Patent: *Oct. 8, 2013

(54) FOOD ADDITIVE FOR RUMINANTS BASED ON EUGENOL AND CINNAMALDEHYDE

(75) Inventors: François Gautier, Seynod (FR); Christopher Kamel, Cessy (FR); Sergio Calsamiglia, San Cugat del Valles (ES); Perry Doane, Decatur (IN)

(73) Assignees: ADM Alliance Nutrition, Inc., Quincy, IL (US); Axiss France S.A.S. (FR)

( * ) Notice: Subject to any disclaimer, the term of this patent is extended or adjusted under 35 U.S.C. 154(b) by 1408 days.

This patent is subject to a terminal disclaimer.

(21) Appl. No.: 11/883,600

(22) PCT Filed: Feb. 3, 2006

(86) PCT No.: PCT/FR2006/000253
§ 371 (c)(1),
(2), (4) Date: Nov. 27, 2007

(87) PCT Pub. No.: WO2006/082326
PCT Pub. Date: Aug. 10, 2006

(65) Prior Publication Data
US 2011/0064864 A1     Mar. 17, 2011

(30) Foreign Application Priority Data
Feb. 3, 2005 (FR) ........................... 05 01489

(51) Int. Cl.
*A23K 1/18* (2006.01)
*A23K 1/16* (2006.01)

(52) U.S. Cl.
USPC ........... 426/544; 426/541; 426/534; 426/635; 426/807

(58) Field of Classification Search
USPC ................ 426/2, 534, 541, 544, 807, 635
See application file for complete search history.

(56) References Cited

U.S. PATENT DOCUMENTS

| | | | |
|---|---|---|---|
| 1,286,742 A | 12/1918 | O'Rouke | |
| 2,921,853 A | 1/1960 | Card et al. | |
| 3,998,974 A | 12/1976 | Zaffaroni et al. | |
| 4,938,149 A | 7/1990 | Lotzer | |
| 5,215,768 A * | 6/1993 | Vinci et al. | 426/74 |
| 5,380,893 A * | 1/1995 | Lajoie | 554/156 |
| 5,425,963 A * | 6/1995 | Lajoie | 426/2 |
| 5,558,889 A | 9/1996 | Rossi | |
| 5,741,508 A | 4/1998 | Katsumi et al. | |
| 5,807,594 A | 9/1998 | King et al. | |
| 5,879,696 A | 3/1999 | Blumberg | |
| 6,616,962 B1 | 9/2003 | Fernandez | |
| 2004/0076659 A1* | 4/2004 | Shelford et al. | 424/442 |
| 2011/0206800 A1 | 8/2011 | Miller | |

FOREIGN PATENT DOCUMENTS

| | | |
|---|---|---|
| EP | 0630577 | 12/1994 |
| EP | 1266578 | 12/2002 |
| GB | 2 118 420 | 11/1983 |
| JP | 11196776 | 7/1999 |
| WO | 9314638 | 8/1993 |
| WO | 9959430 A1 | 11/1999 |
| WO | WO 0069277 A1 * | 11/2000 |
| WO | 02085132 A1 | 10/2002 |
| WO | WO 02/085132 | 10/2002 |
| WO | WO 03/094628 | 11/2003 |
| WO | WO 2004/091307 | 10/2004 |
| WO | 2006081588 | 8/2006 |

OTHER PUBLICATIONS

Maitree Suttajit, "Prevention and Control of Mycotoxins" from the book "Mycotoxin prevention and control in foodgrains", 1989, downloaded from www.fao.org/documents.*
Peter Snyder "Antimicrobial Effects of Spices and Herbs", 3 pages, 1997, downloaded from http://www.hi-tm.com/Documents/Spices.html.*
Masood et al. Letters in Applied Microbio., vol. 18, No. 4, pp. 184-186, 1994.*
Hutjens "Feed Additives: Which, When, and Why", downloaded from www.livestocktrail.illinois.edu., dated Mar. 2002, 13 pages.*
SCA Nutech "Good Guts" downloaded from www.farmingscotland.com, dated Aug. 2003, 2 pages.*
Dairyland Laboratories, Inc. Molds and Mycotoxins, downloaded from www.dairylandlabs.com, dated Feb. 2003, 4 pages.*
Sinha et al. Letters in Applied Microb. 1993, vol. 16, pp. 114-117.*
Juglal et al. Australian Mycotoxin Newsletter, vol. 13(3), Sep. 2003, p. 2 of 13.*
Jayashree et al. Australian Mycotoxin Newsletter, vol. 10(3), Sep. 1999, p. 9 of 12.*
El-Baroty et al. African J Biochem Res, vol. 4(6), pp. 167-174, Jun. 2010.*
Machine translation of JP11196776A.*
Cardozo, P.W.;Calsamiglia, S.; Ferret, A.; Kamel, C., "Effects of Natural Plant Extracts on Ruminal Protein Degradation and Fermentation Profiles in Continuous Culture," Journal of Animal Science, 2004, vol. 82, pp. 3230-3236.
Belitz HD; Grosch, W. "Food Chemistry", 1999 Springer Verlag, Berlin, p. 908.
Bullerman L.B., Lieu F.Y., Seier, S.A., "Inhibition of Growth and AFLA Toxin Production by Cinnamon and Clove Oils Cinnamic Aldehyde and Eugenol", Journal of Food Science, 1977, vol. 42, No. 4, pp. 1107-1109.
Pessoa, L.M., et al., "Antihelminthic activity of essential oil of *Ocimum gratissimum* Linn. and Eugenol against *Haemonchus contortus*", Veterinary Parasitology, Elsevier Science, Amsterdam, NL, 2002, vol. 109, pp. 59-63.

(Continued)

*Primary Examiner* — Chhaya Sayala
(74) *Attorney, Agent, or Firm* — Andrew F. Nilles

(57) ABSTRACT

The invention concerns a composition based on a mixture of eugenol and cinnamaldehyde, as food additive for feeding ruminants. The composition may be incorporated in a food additive, or a salt block. The eugenol and the cinnamaldehyde may be natural or identical natural constituents. Administering the composition or the food additive increases meat production and milk production.

5 Claims, No Drawings

(56) References Cited

OTHER PUBLICATIONS

Tilley, J.M.; Terry, R.A., A two stage technique for the in vitro digestion of forage crops. Journal of the British Grassland Society, 1963, vol. 18(2), pp. 104-111.
Van Soest, P.J.; Robertson, J.B.; Lewis, B.A., "Methods for dietary fiber, neutral detergent fiber and non-starch polysaccharides in relation to animal nutrition", 1991, Journal of Dairy Science, vol. 74(10), pp. 3583-3597.
Backgrounding Feeder Calves, Kirkeide, M.A., et al. Sep. 1983, Coop. Ext Serv., downloaded from the internet at http://library.ndsu.edu/tools/dspace/laod/?file=/repository/bitstream/handle/10365/17210/AS-568-1983.pdf?sequence=1.
Xtract website launch announcement downloaded from the internet at http://www.pancosma.com/newsletter_archive/Issue2_2006/02.html, downloaded Jul. 2, 2010.
Ilsley, S. et al., Herbal Sow Diets boost preweaning growth, Feed Mix 10:3(2002) 24-25.
Isley et al., Plant extracts as supplements for lactating sows; effects piglet performance, sow food intake and diet digestibility, Animal Science 77 (2003) 247.
Orndoff et al., "Comparison of Prophylactic or Therapeutic Dietary Administration of Capsaicin for Reduction of *Salmonella* in Broiler Chickens", Avian Diseases, 2005, 49: pp. 527-533.
Platel et al., "Influence of Dietary Spices or their Active Principles on Digestive Enzymes of Small Intestinal Mucosa in Rats", International Journal of Food Science and Nutrition, 1996, 47: pp. 55-59.
Ilsley, S.E. et al., "Plant extracts for sows and suckling piglets", Feed Mix, 12(4), 2004, 24-27.
Zygmunt P.M. et al., "Vanilloid receptors on sensory nerves mediate the vasodilator action of anandamide", Nature. 1999. 400(6743): 452-45.
Extract From research to commercial success, in P&A Marketing News Col. 3, No. 1, 2003, 4-5, available at http://www.pancosma.com/pdf/News03.pdf (last visited Mar. 15, 2006).
Marketing Pamphlet entitled "EXTRACT: When Performance Comes Naturally", distributed by Pancosma & Associates Marketing, Switzerland, available at www.pancosma.com/pdf/axiss4.pdf (last visited Mar. 15. 2005).
Rhodes, M.T., et al., "Reduced Blood Flow to Peripheral and Core Body Tissues in Sheep and Cattle Induced by Endophyte-Infected Tall Fescue," *Journal of Animal Science*, 1991, 69: 2003-2043.
McElroy, A, et al., "Effect of Prolonged Administration of Dietary Capsaucin on Broiler Growth and *Salmonella enteritidis* Suspectability" Avian Diseases, 1994; 88(2): 329-33.
Price, J., "Endometriosis; A Nutritional approach,"available at www.positivehealth.com/article-abstract.php?articled=92 (last visited Dec. 15, 2005).
Socha, M. et al., "Study Shows That Your Heifers Need Avalia® 4 Too," DAIRYNOW, Issue 4, 2004.
Simeone, A. "Comparison of Two Ammoniation Procedures to Reduce the Toxicity of Endophyte-Infected Tall Fescue Seed Fed to Rats," *Drug and Chemical Toxicology*, 1998, 21(3): 387-404.
"MasterGain Fescue Endo-Fighter Minerals" ADM Alliance Nutrition, available at http://www.admani.com//alliancebeef/TechnicalEdge/EndoFighter.htm (last visited Jan. 5, 2006).
"Rumensin Premix, " Material Safety Data Sheet, ELANCO, available at http://www.elanco.us/products/rumensin.htm (last visited Jan. 5, 2006).
"Covotek™ 571," Data Sheet, Prince Agri Products, Inc., available at http://www.pro-ag.com/default.asp?page=products/covotek571.htm&hd=products (last visited Jan. 5, 2006).
Gourine, A. et al., "Role of Capsaicin-Sensitive Afferents in Fever and Cytokine Responses During Systemic and Local Inflammation in Rats" *NeuroImmunoModulation*, 2001; 9(1): 13-22.
Gibbins, I.L. et al., "Co-Localization of Calcitonin Gene-Related Peptide-Like Immonoreactivity With Substance P in Cutaneous, Vascular and Visceral Sensory Neurons of Guinea Pigs." *Neuroscience Letters*, Jun. 12, 1985; 57(2): 125-30.
Vaishnava, P. et al., "Capsaicin Sensitive-Sansory Nerves and Blood Pressure Regulation." *Curr. Med. Chem.—Cardiovasc. Hematological Agents*, Jun. 2003; 1(2): 177-88.
Mejia, J. et al., "Effects of Neuropeptide Y. Calcitonin Gene-Related Peptide, Substance P, and Capsaicin on Cerebral Arteries in Man and Animals," *J. Neurosurg.* 1988: 69(6): 913-8.
Dib, B. et al., "Rats Desensitized by Capsaicin After Their Food Intake Regulation Especially at Cold Ambient Temperature," *Drugs Exptl. Clin. Res.*, 2005; 31(2):53-8.
Van De Wall, E. et al., "Deafferentation Affects Short-Term But Not Long-Term Control of Food Intake," *Physiology & Behavior*, Mar. 31, 2005; 84(4): 659-67.
Cabanac, M. et al., "The Effect of Capsaicin on Temperature Regulation of the Rat," *Pflugers Archiv.*, Nov. 5, 1976; 366(2-3): 217-21.
Jensen, P. et al., "Field Evaluation of Capsaicin as a Rodent Aversion Agent for Poultry Feed," *Pest Management Science*, Sep. 2003: 59(9): 1007-15.
Hill, N.S. et al., "Urinary Alkaloid Excretion as a Diagnostic Tool for Fescue Toxicosis in Cattle," *J. Vet Diagn Invest*, 2000 (12): 210-217.
Zayachkivska, O. S., et al., "Gastroprotective Effects of Flavonoids in Plant Extracts." *Journal of Physiology and Pharmacology* 2005, 56, Suppl. 1, 219-231.
Gangula, P.R.R. et al., "Mechanisms involved in Calcitonin Gene-Related Peptide-Induced Relaxation in Pregnant Rat Uterine Artery," *Biology of Reproduction* 69, 1635-1641 (2003).
Klukovits, A., et al., "Role of Capsaicin-Sensitive Nerve Fibers in Uterine Contractility in the Rat" *Biology of Reproduction* 70, 184-190 (2004).
Surh, Y-J et al., "Capsaicin, A Double-Edged Sword: Toxicity, Metabolism, and Chemopreventive Potential," *Life Sciences*, vol. 55, No, 22, pp. 1845-1855, 1995.
Jamroz, D. et al., "Use of Active SubStances of Plant Origin in Chicken Diets Based on Maise and Locally Grown Cereals," *British Poultry Science*, Aug. 2005: 46(4): 485-93.
Van Eijndhoven, H.W.F. et al., "Vasodilator Reactivity to Calcitonin Gene-Related Peptide is Increased in Mesenteric Arteries of Rats During Early Pregnancy," *Journal of Vascular Research*, 2003: 40:344-350.
Nagy, I, et el., "The Role of the Vanillfold (Capsaicin) Receptor (TRPV1) in Physiology and Pathology," *European Journal of Pharmacology* 500 (2004) 351-369.
Atkinson, M. et al., "The Effects of Prenatal Capsaicin on the Distribution of Substance P in Developing Primary Afferent Neurons," *Neuroscience Letters*, 35 (1983) 25-29.
Surh, Y-J. et al., "Metabolism of Capsaicinoids: Evidence for Aliphatic Hydroxylation and its Pharmacological Implications," *Life Sciences*, vol. 56, No. 16 pp. PL 305-311, 1995.
"ISO-FUSION Technology," Pancosma, available at http://www.pancosma.com/iso_benefits.html (last visited Jan. 16, 2006).
"ISO-FUSION Technology," Pancosma, available at http://www.pancosma.com/iso_concept.html (last visited Jan. 16, 2006).
"XTRACT® data sheet," Prince Agri Products Inc., available at http://www.princeagri.com (last visited Jan. 5, 2006).
"ISO/FUSION Technology," Pancosma, available at www.axissfr.com (last visited Jan. 16, 2006).
Vanner, S. et al., "Submucosal Secretomotor and Vasodilator Reflexes," *Neurogasiroenterol Motil* (2004) 16 Suppl. 1), 39-43.
Kamel, C. "Natural Plant Extracts: Classical Remedies Bring Madam Animal Production Solutions. In Feed Manufacturing in the Mediterranean Region," *Mediterranean Agronomic Institutes*, 2001, pp. 31-38.
Manzini, S. et al., "Vascular Effects of Capsaicin in Isolated Perfused Rat, Mesenteric Bed," *European Journal of Pharmocology*, Mar. 29, 1988; 148 (2):153-9.

* cited by examiner

FOOD ADDITIVE FOR RUMINANTS BASED ON EUGENOL AND CINNAMALDEHYDE

TECHNICAL FIELD OF THE INVENTION

The invention concerns food additives used in animal nutrition or veterinarian medicine to improve the well being and the zootechnical performance of ruminant animals, for example, in the production of meat and milk.

The favorable effect of food additives containing antibiotics is already well known.

But antibiotics have undesirable side effects, may lead to resistance in germs, and cause an involuntary and unacceptable administration of antibiotics to consumers.

Additionally, substitution additives have been developed containing plant extracts. For example, document JP 11196776 explains that to improve quality, freshness, the preservation capacity of beef and veal meat by administering to cattle, in their feed, an additive combining vitamin E with a plant extract chosen from among a group including black pepper, white pepper, celery seed, coriander, cumin, clove, oregano, sage, thyme, bay leaf, cinnamon, etc Document WO 02/085132 A1 explains that to improve effectiveness in the use of the food by ruminant animals, an additive containing a nonionic surfactant and an antioxidant agent should be added to the feed. The additive changes fermentation in the rumen, favoring the production of propionic acid. The document describes an example in which the food additive may also contain, among other similar substances, eugenol and cinnamaldehyde as a palatants or substances intended to modify the taste.

Document XP 002338115 described the use of a combination of eugenol and cinnamaldehyde as an aromatic agent imitating the flavor of cola, for a use in the food industry.

Document WO 2004/091307 A2 describes food additives intended to provide protection to certain terrestrial or water animals against diseases. There is no example of application in the ruminant animals. Eugenol and cinnamaldehyde are cited among a great number of components as possible additives.

Patent GB 2118 420 A describes food additives used to improve the production of poultry meat. Cinnamaldehyde and eugenol are listed among the many substances that may be used in the composition of an additive. The effect obtained is an improvement in the taste of the meat obtained due to the aromatic qualities of the substances used.

Document EP 0.630.577 A1 explains that to improve the digestibility of food intended for ruminant animals, food additives containing eugenol may be used. Cinnamaldehyde is not listed.

PRESENTATION OF THE INVENTION

The problem suggested by the invention is to improve in an even more significant way the zootechnical performance of ruminants, in particular, meat and/or dairy production, by using other means and without using antibiotics.

This invention results from the surprising observation of a positive synergetic effect between a aromatic phenolic derivative, more specifically, eugenol, in combination with an aromatic aldehyde derivative, more precisely, cinnamaldehyde. Combining the two molecules makes it possible to improve the digestibility of foodstuffs by ruminants, and thus the zootechnical performance of the ruminant animals.

DESCRIPTION OF THE PREFERRED MODES OF IMPLEMENTATION

Thus, according to a first feature, the invention proposes improvement of the digestibility of food by ruminant animals by using an active mixture containing eugenol and cinnamaldehyde.

By ruminants, one understands that it refers to the species of milk cows, cattle, sheep, goats.

By eugenol, one understands that it refers to the identical natural compound obtained by synthesis, or the natural compound preferably of plant origin of the *Eugenia* type, such as *Eugenia caryophyllata*, *Eugenia aromatica* and *Eugenia polyantha* or from the *Syzygium* type plants, such as *Syzygium aromaticum* and *Syzygium polyanthum*.

By cinnamaldehyde, one understands that it refers to the identical natural compound obtained by synthesis, or the natural compound preferably of plant origin of the *Cinnamomum* type, such as *Cinnamomum burmannii*, *Cinnamomum cassia*, *Cinnamomum camphora*, *Cinnamomum loureirii*, *Cinnamomum tamala*, *Cinnamomum osmophloeum*, *Cinnamomum porrectum* and *Cinnamomum verum*.

For a good synergetic effect, the relationship between the respective quantities in weight of eugenol and cinnamaldehyde present in the mixture should preferably be between 0.2 and 5, with the best range being between 1 and approximately 1.8. Eugenol is in this instance dominant.

The eugenol-cinnamaldehyde mixture may be beneficially incorporated into the feed of the animal.

Preferably, the mixture of eugenol and cinnamaldehyde should be added to the feed at a proportion of 1 to 20 ppm (grams per ton) approximately, as compared to the dry matter of the feed, which corresponds to a daily amount of 20 to 400 mg approximately for a daily feed of 20 kg of dry matter.

In accordance with the invention, the eugenol-cinnamaldehyde mixture may be used directly in liquid form.

However, the mixture will preferably be used in the powder form after adsorption or absorption upon a solid particulate substrate. The adsorption or absorption operation may include a reasonable heating phase, without the being detrimental to the effectiveness of the active mixture.

The substrates used for adsorption or absorption of the mixture according to the invention may be those employed classically in the pharmaceutical and food sectors, such as: silica, cellulose, salts, calcium carbonates, alginates, sawdust, gums, hydrogenated fats.

The solid substrate backing for eugenol and cinnamaldehyde should preferably be by proportion at least 5% by weight, and a better solution would be at least 20% by weight of the unit substrate solid-eugenol-cinnamaldehyde.

According to another feature, the invention proposes a process to increase the effectiveness of food use by a ruminant animal, by adding to the feed of the animal a mixture of eugenol and cinnamaldehyde in a suitable quantity to increase the digestibility of the feed.

The eugenol and cinnamaldehyde mixture can advantageously be adsorbed or absorbed on a solid particulate substrate, and then the solid particulate substrate may be added to the feed.

According to another feature, the invention proposes a food additive for ruminant animals, containing, in a dietary carrier, a mixture of eugenol and cinnamaldehyde such as defined above and adsorbed or absorbed upon a solid particulate substrate.

Preferably, the mixture is present with a ratio ranging from between 0.00005% and 5% by weight of the food additive.

In the food additive, the carrier may contain, for example, a vitamin mixture that by weight comprises between 0.1% and 1%, mineral salts at between 20% and 80%, proteins at between 20% and 80%, and flour mill bi-products at between 20% and 80%.

According to another feature, the invention proposes a feed with great digestibility for ruminant animals, containing a mixture of eugenol and cinnamaldehyde with a ratio of approximately 1 to 20 ppm as compared to the dry matter of the feed.

A feed for ruminant animals may contain the eugenol and cinnamaldehyde mixture combined with:
At least 50% cereals,
At least 25% oil-cakes,
At least 20% flour mill bi-products, Preferably, the ratio between the eugenol and cinnamaldehyde mixture present in the feed and the respective quantities by weight of eugenol and cinnamaldehyde will lie between 0.2 and 5; is more beneficial within a range of approximately between 1 and 1.8.

Tests were carried out in order to show the effectiveness of the eugenol-cinnamaldehyde mixture according to the invention, and its beneficial use in improving the zootechnical properties of the ruminant animals. The five studies hereafter show this effectiveness.

Study 1

During this first study, the effects of a mixture according to the invention on the digestibility of the feed of the ruminant animals was analyzed, by conducting an "in vitro" study in accordance with the Tilley and Terry method (1963).

For a more complete description of this method, please refer to the following publication: Tilley, J. M. A. and Terry, R. A. 1963. A two stage technique for the in vitro digestion of forage crops. J. Brit. Grassland Soc. 18-104-111.

For incubation the following was used:
a) The basic feed made up of 100% dehydrated alfalfa, supplemented by an equal amount of Peugenol, or of cinnamaldehyde, or of a mixture of the two components;
b) MacDougall buffer;
c) Liquid taken from the empty rumen of four animals permanently equipped with a nozzle on the level of the rumen and nourished with the basic feed.

In practice, four 250 milliliter containers each containing the liquid from the rumen and the MacDougall buffer in a ratio of 1 to 4, to which 1 gram (dry matter) of the alfalfa was added, all contained in a permeable Dacron sachet.

The ruminated liquid originated in fistulated cows during the first 100 days of lactation. The state of the first container was preserved, without making any addition. In the second container, 30 ppm (parts per million by weight) of eugenol was added. In the third container, 30 ppm cinnamaldehyde was added. In the fourth container, 15 ppm of eugenol and 15 ppm of cinnamaldehyde was added.

The containers were incubated at 39° C. during 24 hours.

The Dacron™ sachets were removed, washed and dried at 55° C.

Various digestibility parameters were determined according to the Van Soest et al. method (1991). For a more complete description of this method, please refer to the following publication: Van Soest, P. J. Robertson, J. D., and Lewis, B. A. 1991. Methods for dietary fibre, neutral détergent fibre and non-starch polysaccharides in relation to animal nutrition. J. Dairy Se. 74: 3583-3597.

Thus, the digestibility, as determined by material disappearance, was measured by evaluating the digestibility of the dry matter (DMd), the digestibility of neutral digestible fiber (NDFd) and the digestibility of acid digestible fiber (ADFd); measurements were made using an ANKOM 200 machine.

The results obtained are summarized in Table 1 below:

| Treatment | Negative control (no additive) | Cinnamaldehyde | Eugenol | Eugenol + Cinnamaldehyde |
|---|---|---|---|---|
| DMd (%) | 37.77 | 39.06 | 40.02 | 40.46 |
| NDFd (%) | 5.60 | 4.83 | 5.63 | 10.08 |
| ADFd (%) | 9.03 | 8.53 | 8.05 | 11.47 |

The table shows that the combination of eugenol and cinnamaldehyde according to the invention notably improves the digestibility of the fibers of the dehydrated alfalfa, which constitutes a key raw material in the milk cow's diet. On the other hand, eugenol alone or the cinnamaldehyde alone does not improve the digestibility of fibers.

Study 2

In the second study, the effect of a variation in the relative proportions of eugenol and cinnamaldehyde in a food additive on the production of meat and the dairy production was tested.

In this test, sixteen Holstein-Freisan milk cows, in their eighth week of lactation, were divided for Latin type Square 4×4 testing. Each period of treatment lasted two weeks.

The first group received a food without an additive.

The second group received a food containing 30 ppm cinnamaldehyde.

The third group received a food containing a mixture of 30 ppm cinnamaldehyde and 15 ppm of eugenol.

The fourth group received a food containing a mixture of 30 ppm eugenol and 15 ppm of cinnamaldehyde.

During each treatment period, the food consumption and the dairy production were measured.

The results obtained are contained in Table 2 below:

| | Treatment | | | |
|---|---|---|---|---|
| | Negative Control (no additive) | Cinnamaldehyde 30 | Cinnamaldehyde 30 + Eugenol 15 | Eugenol 30 + Cinnamaldehyde 15 |
| Food Consumption (kg MS/animal/d) | 3.087a | 2.571b | 2.632b | 3.287a |
| Milk Production (l/animal/d) | 37.28 | 37.23 | 35.76 | 38.35 |

It should be mentioned that a food additive containing cinnamaldehyde alone, or a food additive containing a mixture of cinnamaldehyde and eugenol in which the cinnamaldehyde is distinctly preponderant, leads to a reduction of the food consumption (in kilogram of dry matter per animal/per day), and leads to a reduction in milk production (in liter per animal/per day).

On the other hand, treatment using a food additive in which eugenol is predominant in a mixture of eugenol and cinnamaldehyde led to an increase in food consumption and milk production.

Study 3

This third study consisted in measuring the milk production in the milk cow, according to the presence of or the absence of a food additive containing a mixture of 28% of eugenol and 17% of cinnamaldehyde.

The feed was made of corn, corn silage, soy oil cakes.

The food additive resulted in adding approximately 400 milligrams of the eugenol and cinnamaldehyde mixture, per animal and feed.

The test was performed during the first twelve months of lactation on 173 Holstein cows divided in two groups.

The first group, which was the negative control group, received a complete feed without an additive.

A second group received the same feed supplemented with the combination of eugenol and cinnamaldehyde indicated above.

The results obtained are indicated in Table 3 below:

| Treatment | Control Group (no additive) | Experimental Group (Eugenol + Cinnamaldehyde) |
|---|---|---|
| Number of Animals | 97 | 76 |
| Dry matter Consumption (kg MS/animal/day) | 22.7 | 22.7 |
| Milk Production (kg/animal/day) | 34.2 | 36.1 |
| Protein yield from milk (g/animal/day) | 1259 | 1302 |
| Butter fat yield from milk (g/animal/day) | 983.4 | 1031 |

The result shows a noticeable improvement in milk production through the addition of a food additive according to the invention.

Study 4

The fourth study measures the growth of cattle to meat.

This study was conducted for 75 days under traditional breeding conditions in France using Blonde d'Aquitaine beef stock. The herd was divided into two groups of 15 animals.

The first group, (the negative control group), received a complete feed based on corn silage and grains, without an additive.

The other group, (the experimental group) received the same feed but supplemented with a mixture of eugenol and cinnamaldehyde according to the invention, in a proportion of 28% eugenol and 17% cinnamaldehyde. The dosage was approximately 400 milligrams of the eugenol and cinnamaldehyde mixture, per animal and per feed.

The live weight of the animals was taken at the beginning and then at 75 days.

The results are shown in Table 4 below:

| Treatment | Control Group (no additive) | Experimental Group (Eugenol + Cinnamaldehyde) |
|---|---|---|
| Number of Animals | 15 | 15 |
| Live weight at the beginning (kg/animal) | 218.5 | 219.6 |
| Live weight at 75 days (kg/animal) | 314 | 323 |
| Daily weight gained (kg/animal/day) | 1.27 | 1.39 |

The result shows an increase in the growth rate by weight of the cattle fed with a feed containing a food additive containing eugenol and cinnamaldehyde according to the invention.

Study 5

This fifth study researches the optimal amount of the eugenol-cinnamaldehyde mixture in the feed of ruminant animals. It is again an experimental "in vitro" study, in which the eugenol-cinnamaldehyde mixture was incorporated into certain mixed feeds including fresh oats, alfalfa hay, corn grains, and sunflower seeds.

The chemical characteristics of the feeds are indicated in table 5 below.

| Food | Dried Material | Total Protein | NDF | ADF | Starch |
|---|---|---|---|---|---|
| Oats | 87.0 | ND* | 35.9 | 21.7 | ND |
| Alfalfa Hay | 86.8 | ND | 30.8 | 25.4 | ND |
| TMR | 93.0 | 16.1 | 30.0 | 15.8 | 37.2 |

*ND = Not Determined

In the table above, the characteristics of each food are expressed as a percentage of dry matter, total protein, neutral digestible fiber (NDF), acid digestible fiber (ADF), for the oats, alfalfa, a complete feed (TMR).

In all the tests, the eugenol-cinnamaldehyde mixture was prepared in the proportion of 28% eugenol and 17% cinnamaldehyde.

The effects of a mixture according to the invention on the feed digestibility according to the Tilley and Terry method were analyzed.

The mixture was included in the feeds according to the following proportions of 3, 30 and 300 mg per day and per animal, by using cattle which consume an average of 20 kg of dry matter per day.

A comparison was made between feeds containing sodium-monensin dissolved in ethanol, and those without the eugenol-cinnamaldehyde mixture.

Control bottles were also prepared, containing ethanol, to avoid the parasitic effects of fermentation due to ethanol. The rumen fluid was collected from two cows, which were equipped with nozzles, and which were fed a feed similar to that used in the study.

1 g sample of the dry matter was weighed in three 125 ml capacity bottles, and three additional bottles were used for negative control containing only a buffer solution and a ruminated fluid, for the correction. 10 ml of ruminated fluid were added to 40 ml of an anaerobic buffer solution in each bottle. 0.5 g. of each sample inside the filters (ANKOM brand) were weighed, which were then incubated in 250 ml bottles with the ruminated fluid and the buffer solution for 24 hours, added in same proportions as measured gas production.

The results were analyzed by using mixed SAS procedures. The results were compared to the feed containing the monensin. The results from the feed containing monensin were considered a reference result.

The results obtained are contained in Table 6 hereafter which reflects the digestibility of the feeds containing the mixture of eugenol and cinnamaldehyde in doses of 3, 30 and 300 mg per animal/per day (respectively MIX 3, MIX 30, MIX 300) as compared with the digestibility of the feed containing the monensin (MON).

| Treatment | DMd | NDFd | ADFd |
| --- | --- | --- | --- |
| MON | 43.43 | 22.24 | 24.38 |
| MIX3 | 43.96 | 22.16 | 22.55 |
| MIX30 | 45.70 | 26.74 | 27.54 |
| MIX300 | 45.23 | 25.29 | 28.597 |

Thus, this table reflects the digestibility of neutral digestible fiber (NDFd), digestibility of acid digestible fiber (ADFd), and dry matter digestibility (DMd), after 24 hours.

The table shows that the effects of the eugenol-cinnamaldehyde mixture on the digestibility of the dry matter and fibers are no better than those with monensin, due to the low level, (i.e., dose of 3 mg per animal/per day), than a maximum which is obtained with a 30 mg dose per animal/per day, and than an improvement which is then obtained, (although weaker), with a 300 mg dose per animal/per day.

It may be deduced from this comparison that the beneficial daily dose of the eugenol and cinnamaldehyde mixture may lie between 20 and 400 mg per animal/per day for a consumption of 20 kg dry matter. This corresponds to a proportion of 1 to 20 ppm of the eugenol-cinnamaldehyde mixture as compared to the feed's dry matter.

From the studies conducted, it could be determined that an improvement was obtained in the digestibility of food by the action of adding a eugenol and cinnamaldehyde mixture, in which the ratio between the respective quantities by weight of eugenol and cinnamaldehyde should be preferably higher than approximately 0.2 and lower than approximately 5. It appears that more beneficial results are obtained by a mixture in which the ratio between the respective quantities by weight of eugenol and cinnamaldehyde lies between 1 and approximately 1.8. The eugenol and cinnamaldehyde mixture may be used as a food additive. The eugenol and cinnamaldehyde mixture may be beneficial in the food additive in a proportion of 0.00005% and 5% by weight. The carrier that forms the food additive with the mixture above may contain a vitamin mixture that by weight comprises between 0.1% and 1%, mineral salts at between 20% and 80%, proteins at between 20% and 80%, and flour mill bi-products at between 20% and 80%.

According to another application, the mixture may be used to make a lick stone. In this case, the mixture may be associated with mineral salts taken from the magnesium, calcium, phosphorus salt family.

The mixture may also be used to make feed for ruminant animals.

For example, said feed may contain:
the eugenol-cinnamaldehyde mixture defined above,
at least 50% cereals,
at least 25% oil-cakes,
at least 20% flour mill bi-products, This invention is not limited to the modes of implementation which have been explicitly described, but includes various alternatives and generalizations of these contained within the range of the Claims below.

The invention claimed is:

1. A method of increasing milk production in a dairy cow comprising:
    mixing a combination consisting of eugenol and cinnamaldehyde with a feed, wherein the amount of the eugenol and the cinnamaldehyde in the mixture is predominantly the eugenol; and
    feeding the feed to the dairy cow such that the dairy cow receives between 20 to 400 mg of the combination of the eugenol and the cinnamaldehyde per day.

2. The method according to claim 1, further comprising placing the combination of the eugenol and the cinnamaldehyde on a solid, particulate substrate.

3. The method according to claim 1, wherein the combination of the eugenol and the cinnamaldehyde is liquid.

4. The method of claim 1, wherein the feed comprises:
    at least 50% cereals; and
    at least 20% of flour mill by-products.

5. The method of claim 1, wherein the feed comprises:
    0.1 to 1% by weight of a vitamin mixture;
    20% to 80% by weight of mineral salts;
    20% to 80% by weight of protein; and
    20% to 80% by weight of flour mill by-products.

* * * * *